United States Patent [19]
Rondeau et al.

[11] Patent Number: 6,001,135
[45] Date of Patent: *Dec. 14, 1999

[54] COMPOSITIONS AND PROCESSES FOR DYEING KERATIN FIBERS WITH CATIONIC DIRECT DYES, OXIDATION BASES, AND OXIDIZING AGENTS

[75] Inventors: Christine Rondeau, Sartrouville; Jean Cotteret, Verneuil Sur Seine; Roland De La Mettrie, Le Vesinet, all of France

[73] Assignee: L'Oreal, Paris, France

[ * ] Notice: This patent is subject to a terminal disclaimer.

[21] Appl. No.: 08/994,444

[22] Filed: Dec. 19, 1997

[30] Foreign Application Priority Data

Dec. 23, 1996 [FR] France ................................ 96 15895

[51] Int. Cl.$^6$ ...................................................... A61K 7/13
[52] U.S. Cl. ........................ 8/407; 8/408; 8/409; 8/410; 8/426
[58] Field of Search ................ 8/405, 406, 407, 8/408, 409, 410, 423, 426

[56] References Cited

U.S. PATENT DOCUMENTS

| | | | |
|---|---|---|---|
| 3,524,842 | 8/1970 | Grossman et al. | 8/426 |
| 3,578,386 | 5/1971 | Kalopissis et al. | 8/426 |
| 3,869,454 | 3/1975 | Lang et al. | 534/778 |
| 3,955,918 | 5/1976 | Lang | 8/426 |
| 3,985,499 | 10/1976 | Lang et al. | 8/426 |
| 4,025,301 | 5/1977 | Lang | 8/405 |
| 4,425,132 | 1/1984 | Grollier et al. | 8/405 |
| 5,637,115 | 6/1997 | Balzer et al. | 8/407 |
| 5,733,343 | 3/1998 | Mockli et al. | 8/426 |

FOREIGN PATENT DOCUMENTS 0 739 622   10/1996   European Pat. Off. .

*Primary Examiner*—Caroline D. Liott
*Attorney, Agent, or Firm*—Finnegan, Henderson, Farabow, Garrett & Dunner, L.L.P.

[57] ABSTRACT

A ready-to-use composition for the oxidation dyeing of keratin fibers, in particular human keratin fibers such as the hair, this ready-to-use composition comprising at least one oxidation base in combination with at least one selected cationic direct dye and at least one oxidizing agent, as well as to the dyeing process using this ready-to-use composition.

41 Claims, No Drawings

COMPOSITIONS AND PROCESSES FOR DYEING KERATIN FIBERS WITH CATIONIC DIRECT DYES, OXIDATION BASES, AND OXIDIZING AGENTS

The technology involved in this application is related to that disclosed in the following co-pending U.S. applications filed on even date herewith:

(1) Title: COMPOSITION FOR THE OXIDATION DYEING OF KERATIN FIBERS AND DYEING PROCESS USING THIS COMPOSITION Inventors: Christine Rondeau, Jean Cotteret, Roland de la Mettrie Ser. No. 08/994,127, pending (2) Title: COMPOSITION FOR THE OXIDATION DYEING OF KERATIN FIBRES AND DYEING PROCESS USING THIS COMPOSITION Inventors: Christine Rondeau, Jean Cotteret, Roland de la Mettrie Ser. No. 08/994,130, pending (3) Title: COMPOSITION FOR THE OXIDATION DYEING OF KERATIN FIBERS AND DYEING PROCESS USING THIS COMPOSITION Inventors: Christine Rondeau, Jean Cotteret, Roland de la Mettrie Ser. No. 08/994,446, now U.S. Pat. No. 5,879,412.

The specifications of these related applications are hereby specifically incorporated by reference.

The present invention relates to a ready-to-use composition for the oxidation dyeing of keratin fibers, in particular human keratin fibers such as the hair, this composition comprising, in a medium which is suitable for dyeing, at least one oxidation base in combination with at least one selected cationic direct dye and at least one oxidizing agent, as well as to the dyeing process using this composition. The invention also relates to a dyeing kit for the preparation of such a ready-to-use composition.

It is known to dye keratin fibers, and in particular human hair, with dye compositions containing oxidation dye precursors, in particular ortho- or para-phenylenediamines, and ortho- or para-aminophenols, which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being selected in particular from aromatic meta-diamines, meta-aminophenols, meta-diphenols and certain heterocyclic compounds.

The variety of compounds used as regards the oxidation bases and the couplers allows a wide range of colors to be obtained.

It is also known that in order to vary the shades obtained further and to give them glints, it is possible to use, in combination with the oxidation dye precursors and the couplers, direct dyes, that is to say colored substances which provide coloration in the absence of an oxidizing agent.

The so-called "permanent" coloration obtained by means of these oxidation dyes must moreover satisfy a certain number of requirements. Thus, it must allow shades of the desired intensity to be obtained and it must be able to withstand external agents (light, bad weather, washing, permanent waving, perspiration, rubbing).

The great majority of direct dyes belong to the family of nitrobenzene compounds and have the drawback, when they are incorporated into dye compositions, of leading to colorations that have insufficient endurance, i.e., fastness, in particular with respect to shampoos.

The present invention proposes novel compositions for the oxidation dyeing of keratin fibers, and in particular human keratin fibers such as the hair, which make it possible to obtain colorations which are rich with glints and at the same time have good endurance properties.

Thus, the inventors have discovered that it is possible to obtain novel dyes which are both rich with glints and have good endurance, by combining:

at least one oxidation base, at least one cationic direct dye of formulae (I) and/or (II) and/or (III) and/or (III') defined below, and at least one oxidizing agent.

One subject of the invention is thus a ready-to-use composition for the oxidation dyeing of keratin fibers, and in particular human keratin fibers such as the hair, comprising, in a medium which is suitable for dyeing:

at least one oxidation base, at least one cationic direct dye selected from:

a) the compounds of formula (I) below:

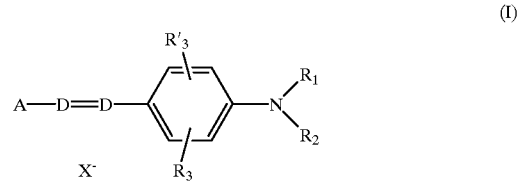

(I)

in which:

D independently represents a nitrogen atom or the —CH group, $R_1$ and $R_2$ each independently represent a hydrogen atom; a $C_1$–$C_4$ alkyl radical which may be substituted with a —CN, —OH or —$NH_2$ radical, or form, with a carbon atom of the benzene ring, a heterocycle which is optionally oxygenated or nitrogenous, which may be substituted with one or more $C_1$–$C_4$ alkyl radicals; or a 4'-aminophenyl radical, $R_3$ and $R'_3$ each independently represents a hydrogen or halogen atom selected from chlorine, bromine, iodine and fluorine, or a cyano, $C_1$–$C_4$ alkoxy or acetyloxy radical, $X^-$ represents an anion preferably selected from chloride, methylsulphate and acetate, A represents a group selected from the structures A1 to A19 below:

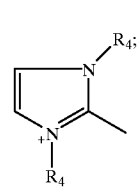

A1

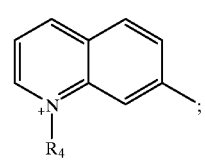

A2

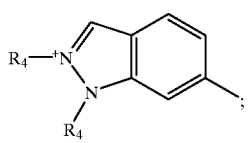  A3
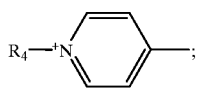  A4
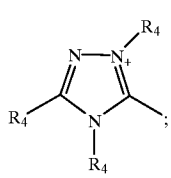  A5
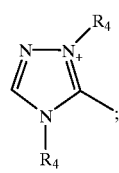  A6
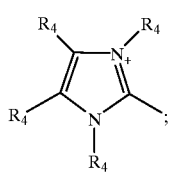  A7
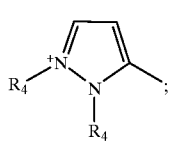  A8
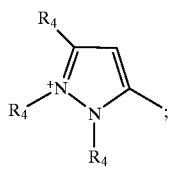  A9
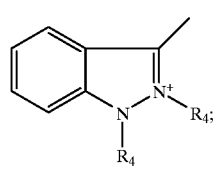  A10
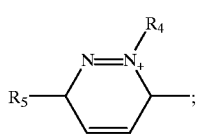  A11
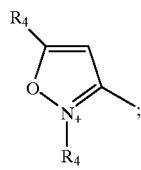  A12
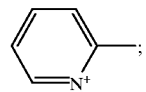  A13
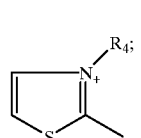  A14
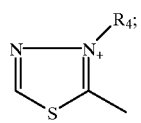  A15
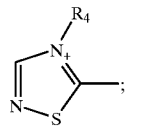  A16
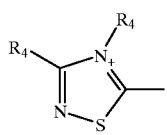  A17
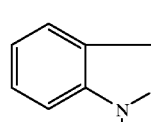  A18
and
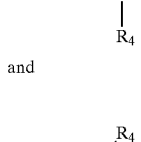  A19
in which:
$R_4$ independently represents a $C_1$–$C_4$ alkyl radical which may be substituted with a hydroxyl radical, and
$R_5$ represents a $C_1$–$C_4$ alkoxy radical,
with the proviso that when D represents —CH, A represents structure A4 or A13 and
$R_3$ is not an alkoxy radical, then $R_1$ and $R_2$ do not simultaneously denote a hydrogen atom;

b) the compounds of formula (II) below:

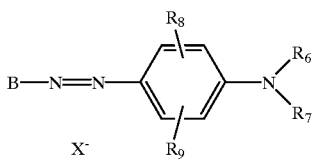

(II)

in which:

$R_6$ represents a hydrogen atom or a $C_1$–$C_4$ alkyl radical, $R_7$ represents a hydrogen atom, an alkyl radical which may be substituted with a —CN radical or with an amino group, a 4'-aminophenyl radical, or forms with $R_6$ a heterocycle which is optionally oxygenated and/or nitrogenous, which may be substituted with a $C_1$–$C_4$ alkyl radical, $R_8$ and $R_9$ each independently represents a hydrogen atom, a halogen atom such as bromine, chlorine, iodine or fluorine, a $C_1$–$C_4$ alkyl or $C_1$–$C_4$ alkoxy radical or a —CN radical, $X^-$ represents an anion preferably selected from chloride, methylsulphate and acetate, B represents a group selected from the structures B1 to B6 below:

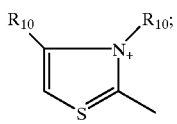

B1

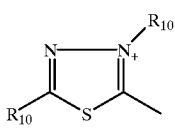

B2

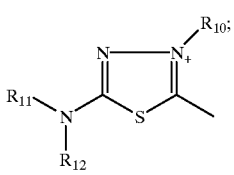

B3

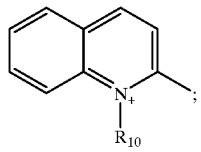

B4

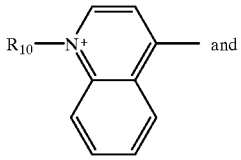

and

B5

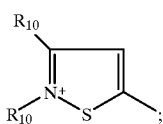

B6 in which:

$R_{10}$ represents a $C_1$–$C_4$ alkyl radical, and $R_{11}$ and $R_{12}$ each independently represents a hydrogen atom or a $C_1$–$C_4$ alkyl radical;

c) the compounds of formulae (III) and (III') below:

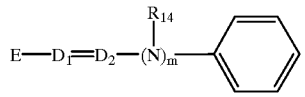

(III)

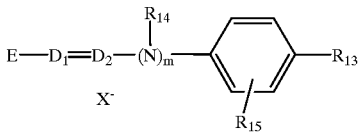

(III)

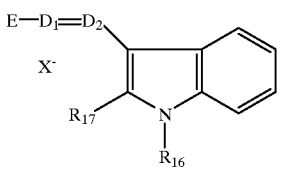

(III')

in which:

$R_{13}$ represents a hydrogen atom, a $C_1$–$C_4$ alkoxy radical, a halogen atom such as bromine, chlorine, iodine or fluorine, or an amino radical, $R_{14}$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups, $R_{15}$ represents a hydrogen or halogen atom such as bromine, chlorine, iodine or fluorine, $R_{16}$ and $R_{17}$ each independently represents a hydrogen atom or a $C_1$–$C_4$ alkyl radical, $D_1$ and $D_2$ each independently represents a nitrogen atom or a —CH group, m=0 or 1, it being understood that when $R_{13}$ represents an unsubstituted amino group, then $D_1$ and $D_2$ simultaneously represent a —CH group and m=0, $X^-$ represents an anion preferably selected from chloride, methylsulphate and acetate, E represents a group selected from the structures E1 to E8 below:

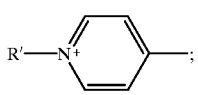

E1

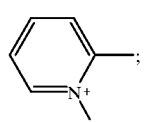

E2

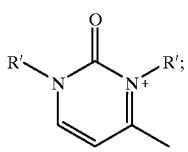

E3

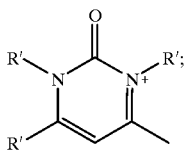 E4

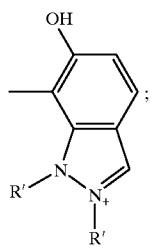 E5

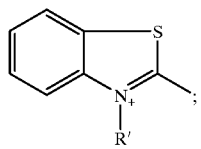 E6

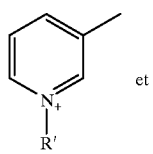 E7

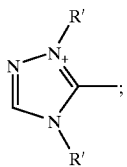 E8 in which:

R' represents a $C_1$–$C_4$ alkyl radical;

when m=0 and $D_1$ represents a nitrogen atom, then E can also denote a group of structure E9 below:

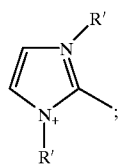 E9 in which:

R' represents a $C_1$–$C_4$ alkyl radical; and at least one oxidizing agent.

The ready-to-use dye compositions in accordance with the invention make it possible to obtain colorations in radiant shades which withstand the various treatments to which the hair may be subjected and in particular with regard to shampoos.

Another subject of the invention is a process for the oxidation dyeing of keratin fibers using this ready-to-use dye composition.

The oxidation base(s) which can be used in the ready-to-use dye compositions in accordance with the invention is (are) preferably selected from para-phenylenediamines, bis (phenyl)alkylenediamines, para-aminophenols, ortho-aminophenols and heterocyclic oxidation bases.

Among the para-phenylenediamines which can be used as oxidation bases in the ready-to-use dye compositions in accordance with the invention, mention may be made in particular of the compounds of formula (IV) below, and the acid-addition salts thereof:

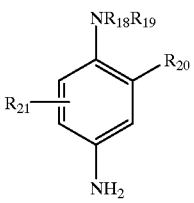 (IV)

in which:

$R_{18}$ represents a hydrogen atom or a $C_1$–$C_4$ alkyl, $C_1$–$C_4$ monohydroxyalkyl, $C_2$–$C_4$ polyhydroxyalkyl, phenyl, 4'-aminophenyl or ($C_1$–$C_4$)alkoxy($C_1$–$C_4$)alkyl radical, $R_{19}$ represents a hydrogen atom or a $C_1$–$C_4$ alkyl, $C_1$–$C_4$ monohydroxyalkyl or $C_2$–$C_4$ polyhydroxyalkyl radical, $R_{20}$ represents a hydrogen atom, a halogen atom such as a chlorine, bromine, iodine or fluorine atom, or a $C_1$–$C_4$ alkyl, $C_1$–$C_4$ monohydroxyalkyl, $C_1$–$C_4$ hydroxyalkoxy, $C_1$–$C_4$ acetylaminoalkoxy, $C_1$–$C_4$ mesylaminoalkoxy or $C_1$–$C_4$ carbamoylaminoalkoxy radical, and $R_{21}$ represents a hydrogen atom or a $C_1$–$C_4$ alkyl radical.

Among the para-phenylenediamines of formula (IV) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine and 2-β-acetylaminoethyloxy-para-phenylenediamine, and the acid-addition salts thereof.

Among the para-phenylenediamines of formula (IV) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid-addition salts thereof are more particularly preferred.

Among the bis(phenyl)alkylenediamines which can be used as oxidation bases in the ready-to-use dye compositions in accordance with the invention, mention may be made in particular of the compounds of formula (V) below, and the acid-addition salts thereof:

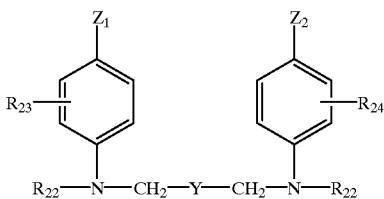

(V)

in which:

$Z_1$ and $Z_2$ each independently represents a hydroxyl radical or $NHR_{25}$ in which $R_{25}$ represents a hydrogen atom or a $C_1$–$C_4$ alkyl radical, $R_{22}$ represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue can be substituted, $R_{23}$ and $R_{24}$ each independently represents a hydrogen or halogen atom or a $C_1$–$C_4$ alkyl radical, Y represents a radical selected from the following radicals: —$(CH_2)_n$—; —$(CH_2)_m$—O—$(CH_2)_m$—; '$(CH_2)m$—CHOH—$(CH_2)_m$— and

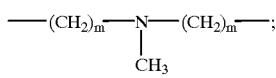

in which:

n is an integer ranging from 0 to 8 and m is an integer ranging from 0 to 4.

Among the bis(phenyl)alkylenediamines of formula (V) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl) ethylenediamine, and the acid-addition salts thereof.

Among these bis(phenyl)alkylenediamines of formula (V), N,N'-bis(β-hydroxyethyl)-N,N'-bis(4'aminophenyl)-1, 3-diaminopropanol or one of the acid-addition salts thereof is particularly preferred.

Among the para-aminophenols which can be used as oxidation bases in the ready-to-use dye compositions in accordance with the invention, mention may be made in particular of the compounds of formula (VI) below, and the acid-addition salts thereof:

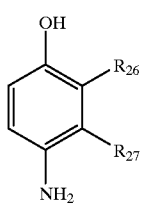

(VI)

in which:

$R_{26}$ represents a hydrogen or fluorine atom or a $C_1$–$C_4$ alkyl, $C_1$–$C_4$ monohydroxyalkyl, $(C_1$–$C_4)$alkoxy$(C_1$–$C_4)$ alkyl, $C_1$–$C_4$ aminoalkyl or hydroxy$(C_1$–$C_4)$alkylamino $(C_1$–$C_4)$alkyl radical, $R_{27}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy $(C_1$–$C_4)$alkyl radical, it being understood that at least one of the radicals $R_{26}$ or $R_{27}$ represents a hydrogen atom.

Among the para-aminophenols of formula (VI) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid-addition salts thereof.

Among the ortho-aminophenols which can be used as oxidation bases in the ready-to-use dye compositions in accordance with the invention, mention may be made more particularly of 2-aminophenol, 2-amino-5-methylphenol, 2-amino-6-methylphenol and 5-acetamido-2-aminophenol, and the acid-addition salts thereof.

Among the heterocyclic bases which can be used as oxidation bases in the ready-to-use dye compositions in accordance with the invention, mention may be made more particularly of pyridine derivatives, pyrimidine derivatives and pyrazole derivatives, and the acid-addition salts thereof.

Among the pyridine derivatives, mention may be made more particularly of the compounds described, for example, in British patents GB 1,026,978 and GB 1,153,196, such as 2,5-diaminopyridine, and the acid-addition salts thereof. The disclosures of GB 1,026,978 and GB 1,153,196 are specifically incorporated by reference herein.

Among the pyrimidine derivatives, mention may be made more particularly of the compounds described, for example, in German patent DE 2,359,399 or Japanese patents JP 88-169,571 and JP 91-333,495, the disclosures of which are specifically incorporated by reference herein, such as 2,4,5, 6-tetraaminopyrimidine and 4-hydroxy-2,5,6-triaminopyrimidine, and the acid-addition salts thereof.

Among the pyrazole derivatives, mention may be made more particularly of the compounds described in German patents DE 3,843,892 and DE 4,133,957 and PCT patent applications WO 94/08969 and WO 94/08970, the disclosures of which are specifically incorporated by reference herein, such as 4,5-diamino-1-methylpyrazole, 3,4-diaminopyrazole and 4,5-diamino-1-(4'chlorobenzyl) pyrazole, and the acid-addition salts thereof.

The acid-addition salts which can be used in the context of the dye compositions of the invention are selected in particular from the hydrochlorides, hydrobromides, sulphates and tartrates.

The cationic direct dyes of formulae (I), (II), (III) and (III') which can be used in the ready-to-use dye compositions in accordance with the invention are known compounds and are described, for example, in patent applications WO 95/01772, WO 95/15144 and EP-A-0,714,954, the disclosures of which are specifically incorporated by reference herein.

Among the cationic direct dyes of formula (I) which can be used in the ready-to-use dye compositions in accordance with the invention, mention may be made more particularly of the compounds corresponding to the structures (I1) to (I52) below:

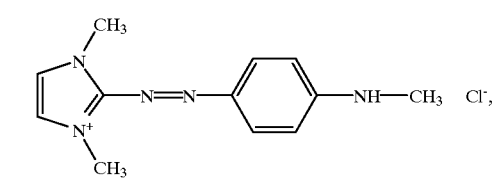 (I1)
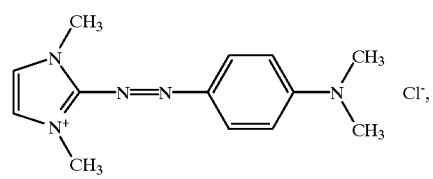 (I2)
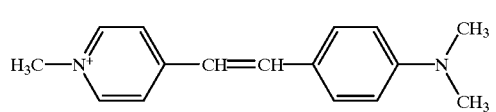 (I3)
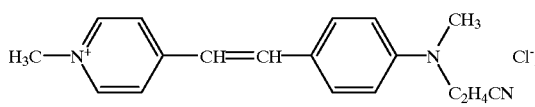 (I4)
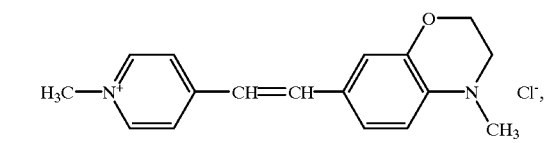 (I5)
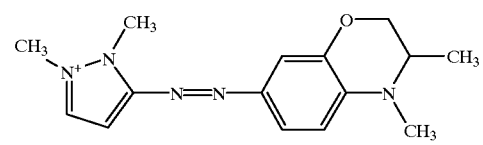 (I6)
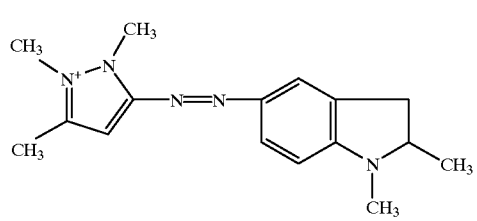 (I7)
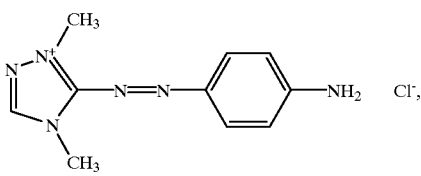 (I10)
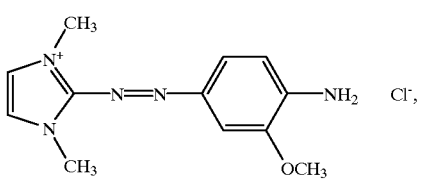 (I11)
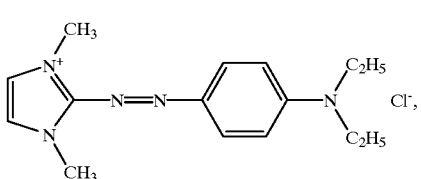 (I12)
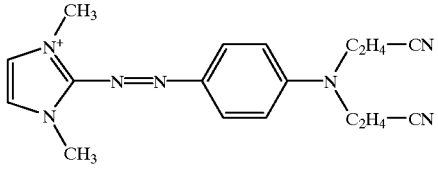 (I13)
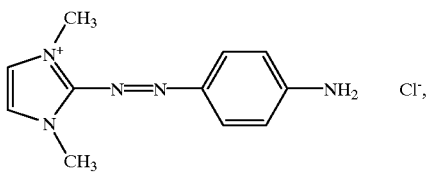 (I14)
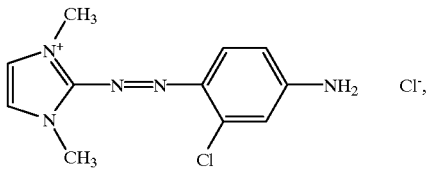 (I15)
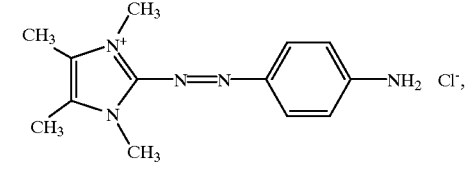 (I16)
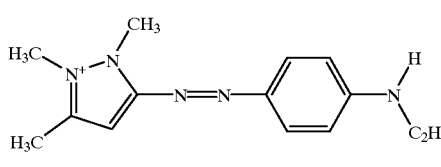 (I17)

-continued
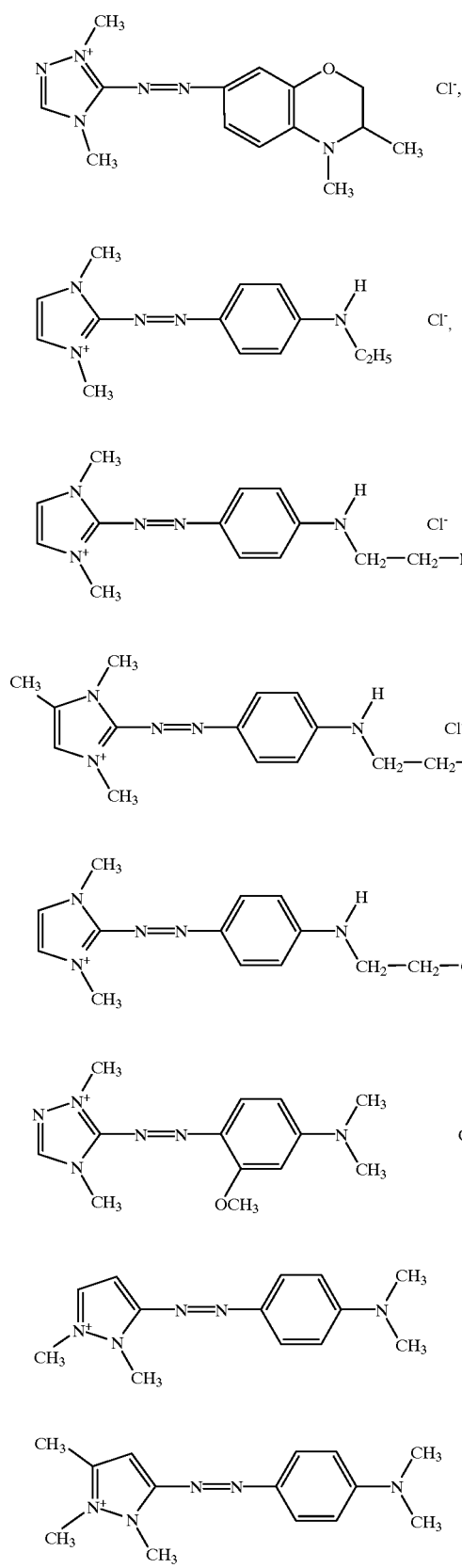
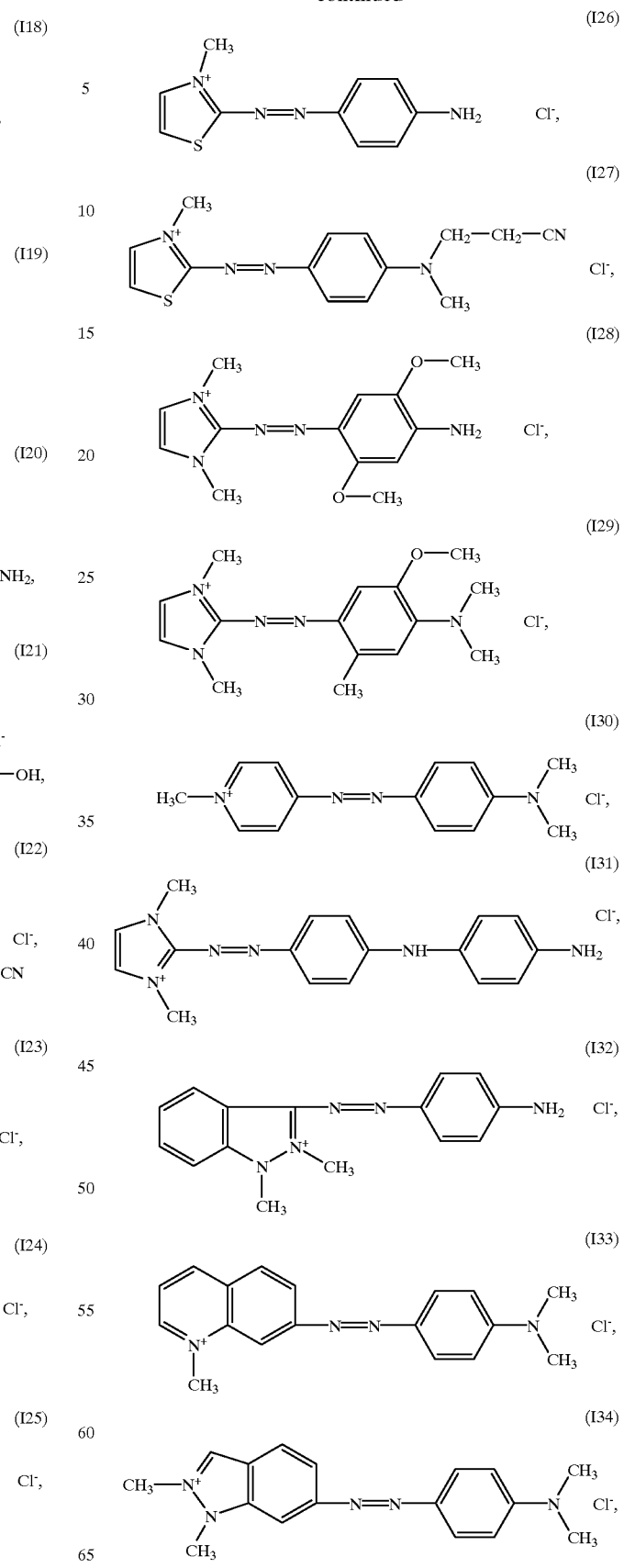

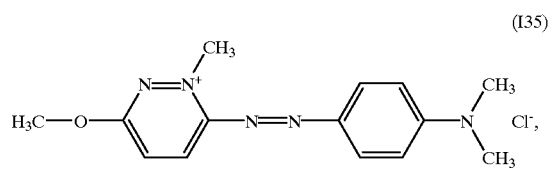 (I35)
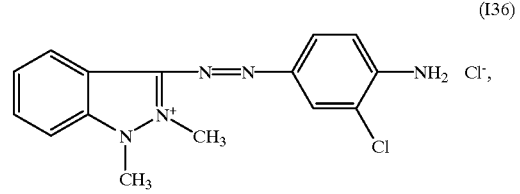 (I36)
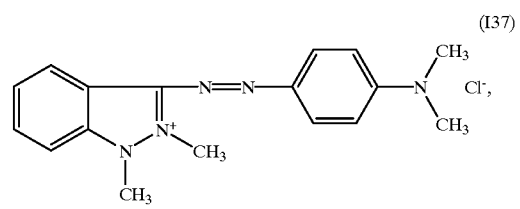 (I37)
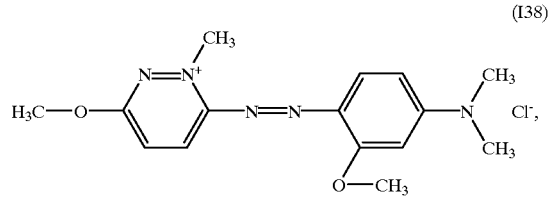 (I38)
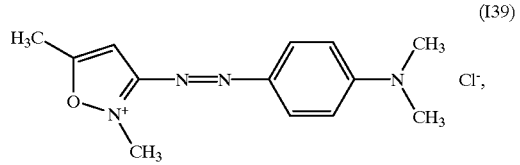 (I39)
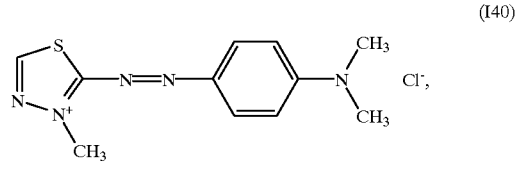 (I40)
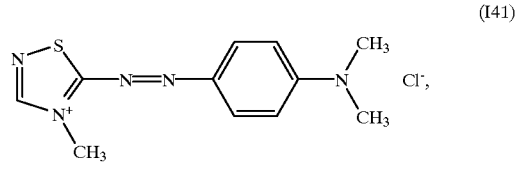 (I41)
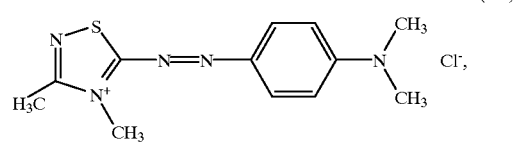 (I42)
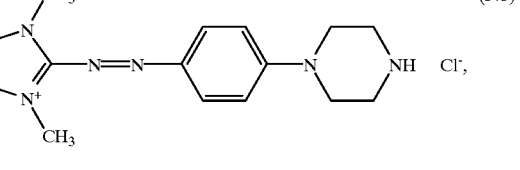 (I43)
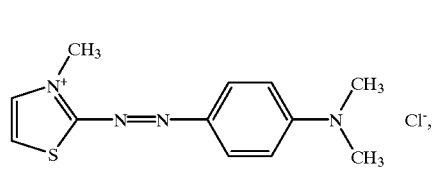 (I44)
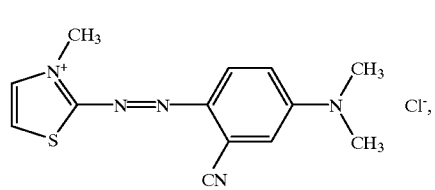 (I45)
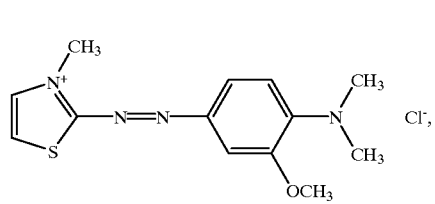 (I46)
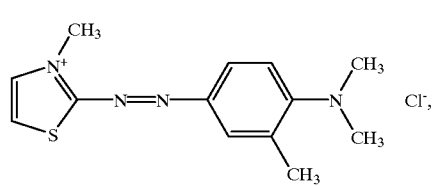 (I47)
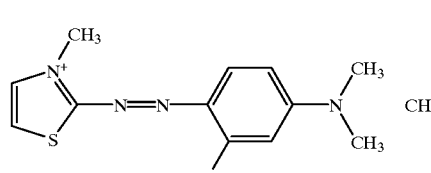 (I48)
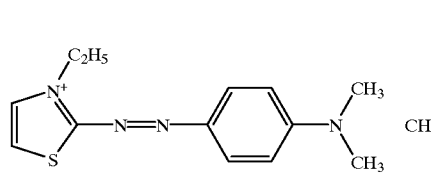 (I49)
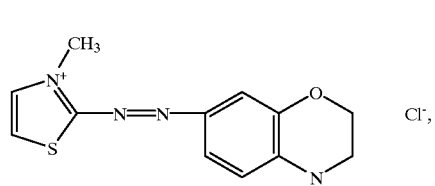 (I50)
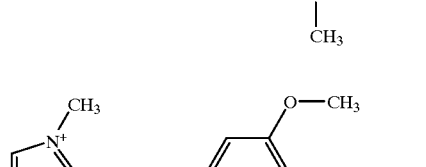 (I51)
and Among the compounds of structures (I1) to (I52) described above, the compounds corresponding to structures (I1), (I2), (I14) and (I31) are more particularly preferred.

Among the cationic direct dyes of formula (II) which can be used in the ready-to-use dye compositions in accordance with the invention, mention may be made more particularly of the compounds corresponding to the structures (II1) to (II12) below:

Among the cationic direct dyes of formula (III) which can be used in the ready-to-use dye compositions in accordance with the invention, mention may be made more particularly of the compounds corresponding to the structures (III1) to (III18) below:

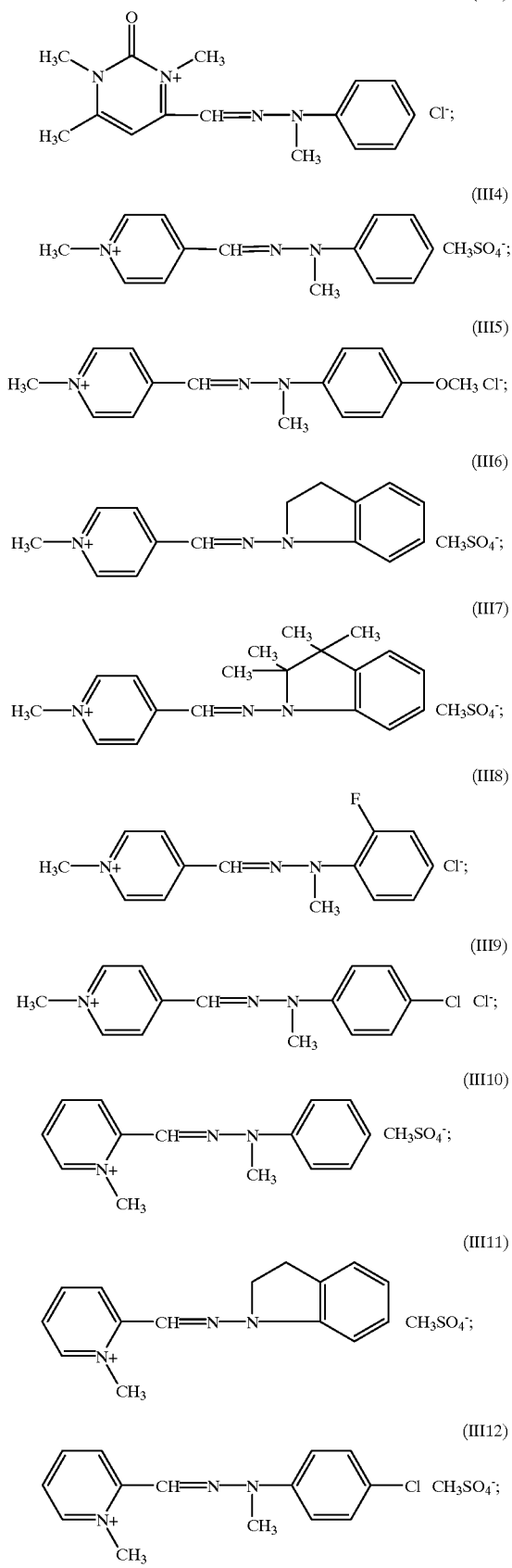
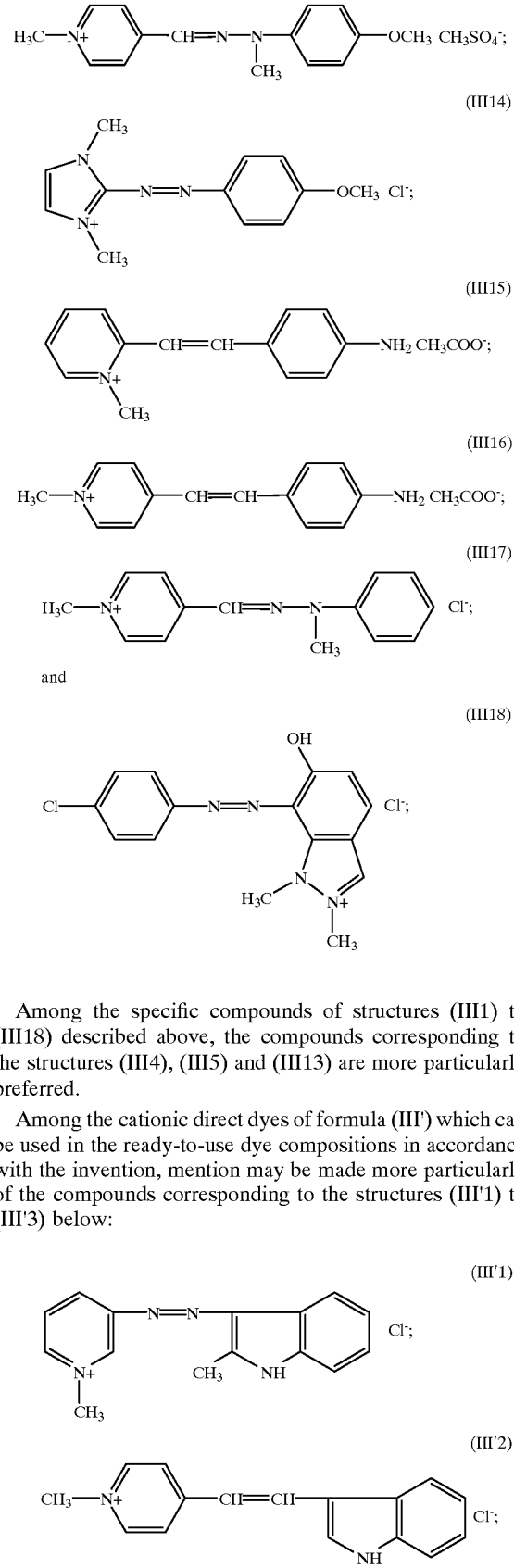

Among the specific compounds of structures (III1) to (III18) described above, the compounds corresponding to the structures (III4), (III5) and (III13) are more particularly preferred.

Among the cationic direct dyes of formula (III') which can be used in the ready-to-use dye compositions in accordance with the invention, mention may be made more particularly of the compounds corresponding to the structures (III'1) to (III'3) below:

-continued and

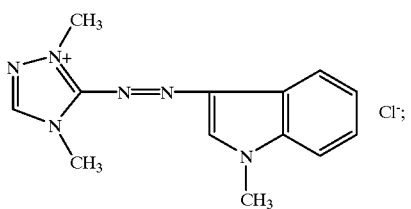
(III'3)

The oxidizing agent present in the dye composition is selected from oxidizing agents used conventionally in oxidation dyeing and preferably from hydrogen peroxide, urea peroxide, alkali metal bromates and persalts such as perborates and persulphates. Hydrogen peroxide is particularly preferred.

The oxidation base(s) are preferably present in a concentration ranging from approximately 0.0001 to approximately 10% by weight relative to the total weight of the ready-to-use dye composition, and even more preferably from approximately 0.001 to approximately 5% by weight relative to the total weight of the ready-to-use dye composition.

The cationic direct dye(s) of formulae (I) and/or (II) and/or (III) and/or (III') in accordance with the invention are preferably present in a concentration ranging from approximately 0.001 to approximately 10% by weight relative to the total weight of the ready-to-use dye composition, and even more preferably from approximately 0.05 to approximately 2% by weight relative to the total weight of the ready-to-use dye composition.

The pH of the dye composition as defined above generally ranges from approximately 5 to approximately 12. It can be adjusted to the desired value using acidifying or basifying agents usually used in the dyeing of keratin fibers.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (VII) below:

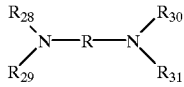
(VII)

in which:

R is a propylene residue optionally substituted with a hydroxyl group or a $C_1$–$C_4$ alkyl radical; and $R_{28}$, $R_{29}$, $R_{30}$ and $R_{31}$ each independently represent a hydrogen atom or a $C_1$–$C_4$ alkyl or $C_1$–$C_4$ hydroxyalkyl radical.

The ready-to-use dye composition in accordance with the invention can also contain, in addition to the oxidation base(s) above and in addition to the cationic dye(s) of formulae (I) and/or (II) and/or (III) and/or (III') above, at least one coupler selected from the couplers usually used for the oxidation dyeing of keratin fibers.

When they are used, the coupler(s) are preferably present in a concentration ranging from approximately 0.0001 to approximately 5% by weight relative to the total weight of the ready-to-use dye composition and even more preferably from approximately 0.005 to approximately 3% by weight relative to the total weight of the ready-to-use dye composition.

In addition to the dyes defined above, the dye composition in accordance with the invention can also contain other direct dyes, in particular in order to modify the shades or to enrich them with glints.

The medium which is suitable for dyeing (or the support) for the ready-to-use dye composition in accordance with the invention generally comprises water or of a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxy-ethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in a concentration preferably ranging from approximately 1 to approximately 40% by weight relative to the total weight of the dye composition, and even more preferably from approximately 5 to approximately 30% by weight relative to the total weight of the dye composition.

The ready-to-use dye compositions in accordance with the invention can also contain various adjuvants used conventionally in compositions for dyeing the hair, such as anionic, cationic, nonionic or amphoteric surfactants or mixtures thereof, anionic, cationic, nonionic or amphoteric polymers or mixtures thereof, inorganic or organic thickeners, antioxidants, penetration agents, sequestering agents, fragrances, buffers, dispersing agents, packaging agents, film-forming agents, preserving agents and opacifiers.

Needless to say, a person skilled in the art will take care to select the optional additional compound(s) mentioned above such that the advantageous properties intrinsically associated with the ready-to-use dye composition in accordance with the invention are not, or are not substantially, adversely affected by the addition(s) envisaged.

The ready-to-use dye compositions in accordance with the invention can be in various forms, such as in the form of liquids, creams or gels or in any other form which is appropriate for dyeing keratin fibers, and in particular human hair.

Another subject of the invention is a process for dyeing keratin fibers, and in particular human keratin fibers such as the hair, using the ready-to-use dye composition as defined above.

According to this process, the ready-to-use dye composition as defined above is applied to the fibers and is left on them for an exposure time preferably ranging from approximately 3 to approximately 40 minutes, more preferably from approximately 5 to approximately 30 minutes, after which the fibers are rinsed, optionally washed with shampoo, rinsed again and dried.

According to a first preferred embodiment, the process includes a preliminary step which involves separately storing, on the one hand, a composition (A) comprising, in a medium which is suitable for dyeing, at least one oxidation base and at least one cationic direct dye selected from the compounds of formulae (I), (II), (III) and (III') as defined above, and, on the other hand, a composition (B) containing, in a medium which is suitable for dyeing, at least one oxidizing agent as defined above, and mixing them together at the time of use before applying this mixture to the keratin fibers.

According to a second preferred embodiment, the process includes a preliminary step which involves separately storing, on the one hand, a composition (A) comprising, in a medium which is suitable for dyeing, at least one oxidation base; on the other hand, a composition (A') comprising, in a medium which is suitable for dyeing, at least one cationic direct dye selected from the compounds of formulae (I), (II), (III) and (III') as defined above, and, lastly, a composition (B) containing, in a medium which is suitable for dyeing, at least one oxidizing agent as defined above, and mixing them together at the time of use before applying this mixture to the keratin fibers.

The composition (A') used according to this second variant of the process in accordance with the invention can optionally be in powder form, the cationic direct dye(s) of formulae (I), (II), (III) and (III') in accordance with the invention itself (themselves) constituting, in this case, all of the composition (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can comprise metal oxides such as titanium oxides, aluminium oxides, kaolin, talc, silicates, mica and silicas.

An advantageous excipient preferred according to the invention is sawdust.

The powdered composition (A') can also contain binders or coating products in an amount which preferably does not exceed approximately 3% by weight relative to the total weight of the said composition (A').

These binders are preferably selected from oils and liquid fatty substances of inorganic, synthetic, animal or plant origin.

The composition (A') can optionally also contain other adjuvants, in powdered form, in particular surfactants of any nature, hair conditioners such as, for example, cationic polymers, etc.

Another subject of the invention is a multi-compartment dyeing "kit" or device or any other multi-compartment packaging system, a first compartment of which contains the composition (A) as defined above, an optional second compartment contains the composition (A') as defined above, when it is present, and a third compartment contains the oxidizing composition (B) as defined above. These devices can be equipped with means which allow the desired mixture to be applied to the hair, such as the devices described in French patent FR-2,586,913, the disclosure of which is specifically incorporated by reference herein.

The examples which follow are intended to illustrate the invention without, however, limiting its scope.

EXAMPLE 1

Composition 1 (A) below, in accordance with the invention, was prepared (content in grams):

| COMPOSITION | 1(A) |
|---|---|
| Para-phenylenediamine | 0.7 |
| Cationic dye of structure (12) | 0.5 |
| Common dye support (*) | (*) |
| Water qs | 100 g |

(*) Common dye support:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name ETHOMEEN O12 by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% $NH_3$ | 10.0 g |

Composition 1(A) was mixed, at the time of use, with an equal amount of a composition (B) containing a 20-volumes hydrogen peroxide solution (6% by weight).

The resulting composition (ready-to-use composition in accordance with the invention) was applied for 30 minutes to locks of natural grey hair containing 90% white hairs. The locks of hair were then rinsed, washed with a standard shampoo and then dried.

The hair was dyed in an intense red shade which showed good endurance properties with respect to subsequent shampooing.

According to a variant of the invention, the cationic direct dye of structure (12) is introduced at the time of use into composition 1(A).

EXAMPLE 2

Composition 2(A) below was prepared:

| | |
|---|---|
| Para-toluylenediamine sulphate | 0.5 g |
| Common dye support as described in Example 1 | (*) |
| Demineralized water qs | 100 g |

Composition 2(A') below was prepared:

| | |
|---|---|
| Cationic dye of structure (I14) | 4 g |
| Quaternary polyammonium sold under the trade name Celquat SC-240 by the company National Starch | 10 g |
| Sawdust qs | 100 g |

One part by weight of composition 2(A) above was mixed, at the time of use, with 0.1 part by weight of composition 2(A') and with one part by weight of a composition (B) containing a 20-volumes hydrogen peroxide solution (6% by weight).

The resulting composition was applied for 30 minutes to locks of natural grey hair containing 90% white hairs. The hair was then rinsed, washed with a standard shampoo and then dried.

The hair was dyed in an intense coppery shade which had very good endurance properties with respect to subsequent shampooing.

We claim:

1. A ready-to-use composition for the oxidation dyeing of keratin fibers, comprising, in a medium suitable for dyeing:

at least one oxidation base, at least one cationic direct dye (a), (b) or (c), wherein (a), (b) and (c) are defined as follows:

a) the compounds of formula (I) below:

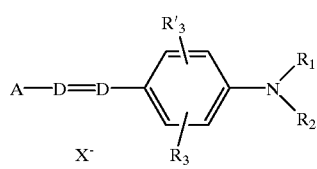

(I)

in which:

D independently represents a nitrogen atom or a —CH group, $R_1$ and $R_2$ each independently represents a hydrogen atom; a $C_1$–$C_4$ alkyl radical which may be substituted with a —CN, —OH or —NH$_2$ radical, or form, with a carbon atom of the benzene ring, a heterocycle which is optionally oxygenated or nitrogenous, which may be substituted with one or more $C_1$–$C_4$ alkyl radicals; or a 4'-aminophenyl radical, $R_3$ and $R'_3$ each independently represents a hydrogen or halogen atom, or a cyano, $C_1$–$C_4$ alkoxy or acetyloxy radical, $X^-$ represents chloride, methylsulphate or acetate, A represents a group having a structure corresponding to one of structures A1 to A19:

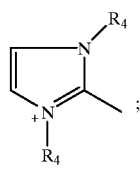
A1

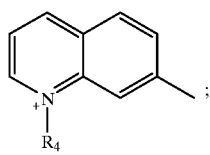
A2

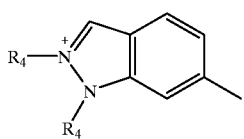
A3

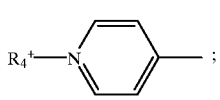
A4

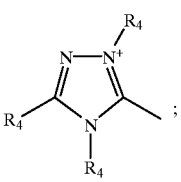
A5

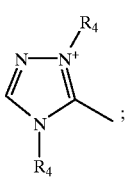
A6

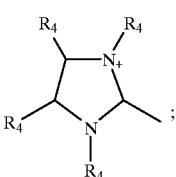
A7

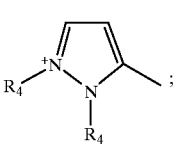
A8

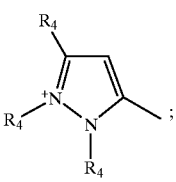
A9

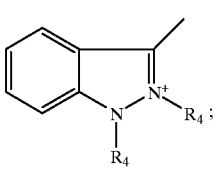
A10

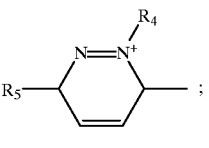
A11

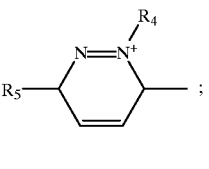
A12

-continued

A13
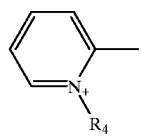

A14
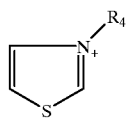

A15
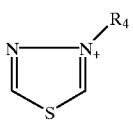

A16
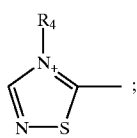

A17
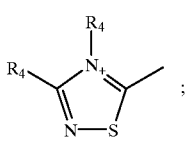

A18
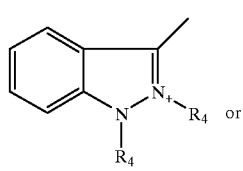  or

A19
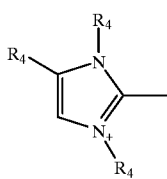

in which

R$_4$ represents a C$_1$–C$_4$ alkyl radical which may be substituted with a hydroxyl radical and R$_5$ represents a C$_1$–C$_4$ alkoxy radical, wherein when D represents —CH, A represents structure A4 or A13 and R$_3$ is not an alkoxy radical, then R$_1$ and R$_2$ do not simultaneously denote a hydrogen atom;

b) the compounds of formula (II) below:

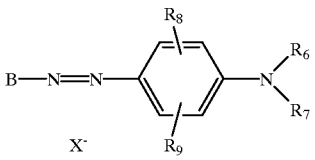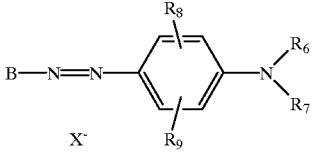

(II)

in which:

R$_6$ represents a hydrogen atom or a C$_1$–C$_4$ alkyl radical,

R$_7$ represents a hydrogen atom, an alkyl radical which may be substituted with a —CN radical or with an amino group, a 4'-aminophenyl radical, or forms with R$_6$ a heterocycle which is optionally oxygenated and/or nitrogenous, which may be substituted with a C$_1$–C$_4$ alkyl radical, R$_8$ and R$_9$ each independently represents a hydrogen atom, a halogen atom, a C$_1$–C$_4$ alkyl or C$_1$–C$_4$ alkoxy radical or a —CN radical, X$^-$ represents chloride, methylsulphate or acetate, B represents a group having a structure corresponding to structures B1 to B6:

B1
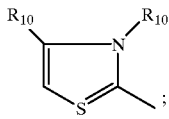

B2
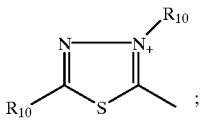

B3
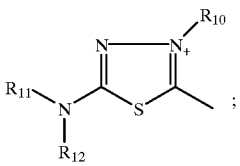

B4
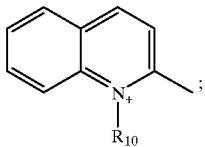

B5
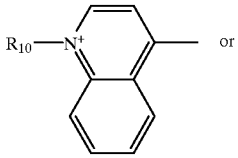  or

B6
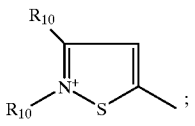

in which:

$R_{10}$ represents a $C_1$–$C_4$ alkyl radical, $R_{11}$ and $R_{12}$ each independently represent a hydrogen atom or a $C_1$–$C_4$ alkyl radical;

c) the compounds of formulae (III) or (III') below:

$$E—D_1{=}D_2—(N)_{\overline{m}}\text{—}\underset{R_{15}}{\underset{|}{\bigcirc}}—R_{13} \quad \overset{R_{14}}{|} \quad X^- \tag{III}$$

$$E—D_1{=}D_2\text{—indole}(R_{17}, R_{16}) \quad X^- \tag{III'}$$

in which:

$R_{13}$ represents a hydrogen atom, a $C_1$–$C_4$ alkoxy radical, a halogen atom, or an amino radical, $R_{14}$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups, $R_{15}$ represents a hydrogen or halogen atom, $R_{16}$ and $R_{17}$ each independently represent a hydrogen atom or a $C_1$–$C_4$ alkyl radical, $D_1$ and $D_2$ each independently represent a nitrogen atom or a —CH group, m=0 or 1, wherein when $R_{13}$ represents an unsubstituted amino group, then $D_1$ and $D_2$ simultaneously represent a —CH group and m=0, $X^-$ represents chloride, methylsulphate or acetate, E represents a group having a structure corresponding to structures E1 to E8:

E1: pyridinium with R'—N+

E2: 2-methylpyridinium with N+—R'

E3: pyrimidinone with R', R'

E4: pyrimidinone with R', R'

E5: hydroxy-methyl-indazolium with R', R'

E6: benzothiazolium with R'

E7: 3-methylpyridinium with R' or

E8: pyrazolium with R', R' in which:

R' represents a $C_1$–$C_4$ alkyl radical;

and wherein when m=0 and $D_1$ represents a nitrogen atom, then E can also denote a group of structure E9:

E9: imidazolium with R', R' in which:

R' represents a $C_1$–$C_4$ alkyl radical; and at least one oxidizing agent.

2. A ready-to-use composition according to claim 1, wherein said keratin fibers are human hair.

3. A ready-to-use composition according to claim 1, wherein with respect to $R_3$, $R'_3$, $R_8$, $R_9$, $R_{13}$, and $R_{15}$, said halogen atom is chlorine, bromine, iodine or fluorine.

4. A ready-to-use composition according to claim 1, wherein said at least one oxidation base is a para-phenylenediamine, bis(phenyl)alkylenediamine, para-aminophenol, ortho-aminophenol, heterocyclic oxidation base or an acid-addition salt of the foregoing.

5. A ready-to-use composition according to claim 4, wherein said paraphenylenediamine has a structure corresponding to formula (IV), or an acid-addition salt thereof:

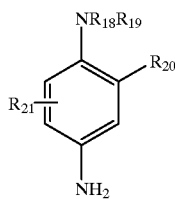
(IV)

in which:

R$_{18}$ represents a hydrogen atom or a C$_1$–C$_4$ alkyl, C$_1$–C$_4$ monohydroxyalkyl, C$_2$–C$_4$ polyhydroxyalkyl, phenyl, 4'-aminophenyl or (C$_1$–C$_4$)alkoxy(C$_1$–C$_4$)alkyl radical, R$_{19}$ represents a hydrogen atom or a C$_1$–C$_4$ alkyl, C$_1$–C$_4$ monohydroxyalkyl or C$_2$–C$_4$ polyhydroxyalkyl radical, R$_{20}$ represents a hydrogen atom, a halogen atom, or a C$_1$–C$_4$alkyl, C$_1$–C$_4$ monohydroxyalkyl, C$_1$–C$_4$ hydroxyalkoxy, C$_1$–C$_4$ acetylaminoalkoxy, C$_1$–C$_4$ mesylaminoalkoxy or C$_1$–C$_4$ carbamoylaminoalkoxy radical, R$_{21}$ represents a hydrogen atom or a C$_1$–C$_4$ alkyl radical.

6. A ready-to-use composition according to claim 5, wherein with respect to R$_{20}$, said halogen atom is chlorine, bromine, iodine or fluorine.

7. A ready-to-use composition according to claim 5, wherein said paraphenylenediamine is:

para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
2,5-dimethyl-para-phenylenediamine,
N,N-dimethyl-para-phenylenediamine,
N,N-diethyl-para-phenylenediamine,
N,N-dipropyl-para-phenylenediamine,
4-amino-N,N-diethyl-3-methylaniline,
N,N-bis(β-hydroxyethyl)-para-phenylenediamine,
4-amino-N,N-bis(β-hydroxyethyl)-3-methylaniline,
4-amino-3-chloro-N,N-bis(β-hydroxyethyl)aniline,
2-β-hydroxyethyl-para-phenylenediamine,
2-fluoro-para-phenylenediamine,
2-isopropyl-para-phenylenediamine,
N-(β-hydroxypropyl)-para-phenylenediamine,
2-hydroxymethyl-para-phenylenediamine,
N,N-dimethyl-3-methyl-para-phenylenediamine,
N,N-(ethyl-β-hydroxyethyl)-para-phenylenediamine,
N-(β,γ-dihydroxypropyl)-para-phenylenediamine,
N-(4'-aminophenyl)-para-phenylenediamine,
N-phenyl-para-phenylenediamine,
2-β-hydroxyethyloxy-para-phenylenediamine,
2-β-acetylaminoethyloxy-para-phenylenediamine,
or an acid-addition salt thereof.

8. A ready-to-use composition according to claim 7, wherein said paraphenylenediamine is:

para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
N,N-bis(β-hydroxyethyl)-para-phenylenediamine,
2-β-hydroxyethyl-para-phenylenediamine,
2-isopropyl-para-phenylenediamine,
2-β-hydroxyethyloxy-para-phenylenediamine, or an acid-addition salt thereof.

9. A ready-to-use composition according to claim 4, wherein said bis(phenyl)alkylenediamines is a compound of formula (V), or an acid-addition salt thereof:

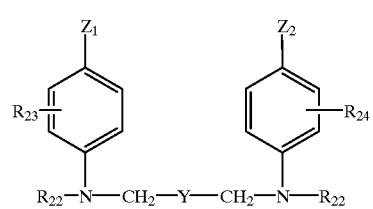
(V)

in which:

Z$_1$ and Z$_2$ each independently represent a hydroxyl radical or NHR$_{25}$ in which R$_{25}$ represents a hydrogen atom or a C$_1$–C$_4$ alkyl radical, R$_{22}$ independently represents a hydrogen atom or a C$_1$–C$_4$ alkyl, C$_1$–C$_4$ monohydroxyalkyl or C$_2$–C$_4$ polyhydroxyalkyl radical or a C$_1$–C$_4$ aminoalkyl radical having an amino residue, in which the amino residue can be substituted, R$_{23}$ and R$_{24}$ each independently represents a hydrogen or halogen atom or a C$_1$–C$_4$ alkyl radical, Y represents one of the following radicals:
—(CH$_2$)$_n$—; —(CH$_2$)$_m$—O—(CH$_2$)$_m$—; —(CH$_2$)m—CHOH—(CH$_2$)$_m$— or

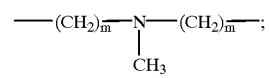

in which:

n is an integer ranging from 0 to 8 and m is an integer ranging from 0 to 4.

10. A ready-to-use composition according to claim 9, wherein said bis(phenyl)alkylenediamine is:

N,N'-bis(β-hydroxyethyl)-N,N'-bis(4'-aminophenyl)-1,3-diaminopropanol,
N,N'-bis(β-hydroxyethyl)-N,N'-bis(4'-aminophenyl) ethylenediamine,
N,N'-bis(4-aminophenyl)tetramethylenediamine,
N,N'-bis(β-hydroxyethyl)-N,N'-bis(4-aminophenyl) tetramethylenediamine,
N,N'-bis(4-methylaminophenyl)tetramethylenediamine,
N,N'-bis(ethyl)-N,N'-bis(4'-amino-3'-methylphenyl) ethylenediamine, or an acid-addition salt thereof.

11. A ready-to-use composition according to claim 10, wherein said bis(phenyl)alkylenediamine is N,N'-bis(β-hydroxyethyl)-N,N'-bis(4'-aminophenyl)-1,3-diaminopropanol or an acid-addition salt thereof.

12. A ready-to-use composition according to claim 4, wherein said para-aminophenol is a compound of formula (VI), or an acid-addition salt thereof:

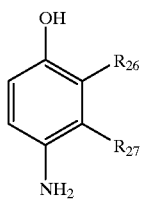

(VI)

in which:

R$_{26}$ represents a hydrogen or fluorine atom or a C$_1$–C$_4$ alkyl, C$_1$–C$_4$ monohydroxyalkyl, (C$_1$–C$_4$)alkoxy(C$_1$–C$_4$)alkyl, C$_1$–C$_4$ aminoalkyl or hydroxy(C$_1$–C$_4$)alkylamino(C$_1$–C$_4$)alkyl radical, R$_{27}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl radical, wherein at least one of the radicals R$_{26}$ or R$_{27}$ represents a hydrogen atom.

13. A ready-to-use composition according to claim 12, wherein said para-aminophenol is:
para-aminophenol,
4-amino-3-methylphenol,
4-amino-3-fluorophenol,
4-amino-3-hydroxymethylphenol,
4-amino-2-methylphenol,
4-amino-2-hydroxymethylphenol,
4-amino-2-methoxymethylphenol,
4-amino-2-aminomethylphenol,
4-amino-2-(β-hydroxyethylaminomethyl)phenol,
4-amino-2-fluorophenol,
or an acid-addition salt thereof.

14. A ready-to-use composition according to claim 4, wherein said ortho-aminophenol is 2-aminophenol, 2-amino-5-methylphenol, 2-amino-6-methylphenol, 5-acetamido-2-aminophenol, or an acid-addition salts thereof.

15. A ready-to-use composition according to claim 4, wherein said heterocyclic oxidation base is a pyridine derivative, a pyrimidine derivative, a pyrazole derivative, or an acid-addition salt thereof.

16. A ready-to-use composition according to claim 4, wherein said acid-addition salt is a hydrochloride, a hydrobromide, a sulphate or a tartrate.

17. A ready-to-use composition according to claim 1, wherein said at least one cationic direct dye of formula (I) is a compound corresponding to one of structures (I1) to (I52):

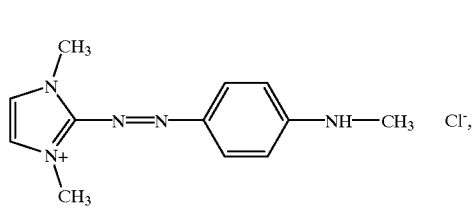

(I1)

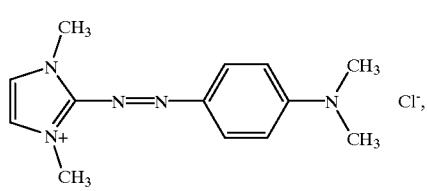

(I2)

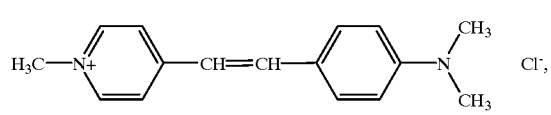

(I3)

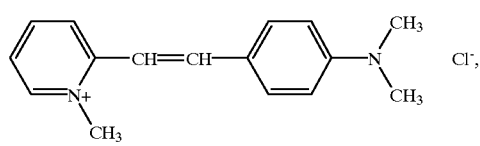

(I4)

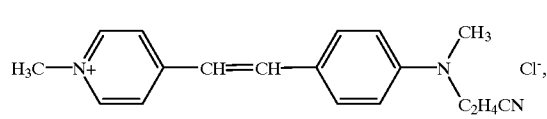

(I5)

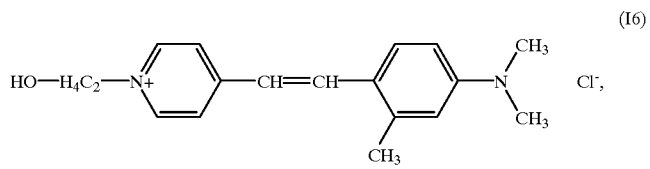
(I6)
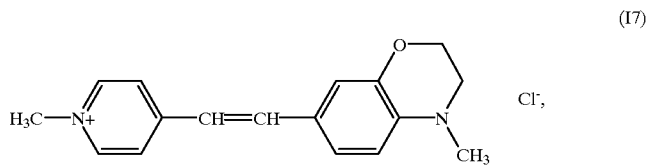
(I7)
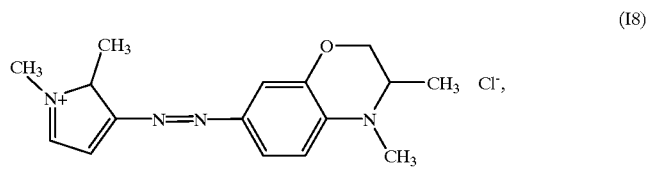
(I8)
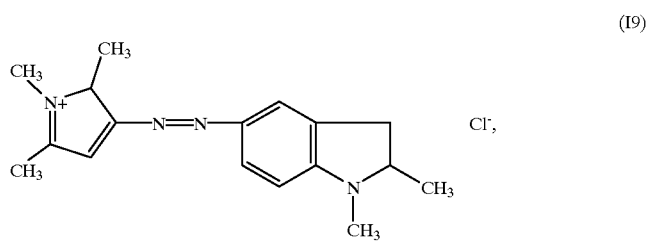
(I9)
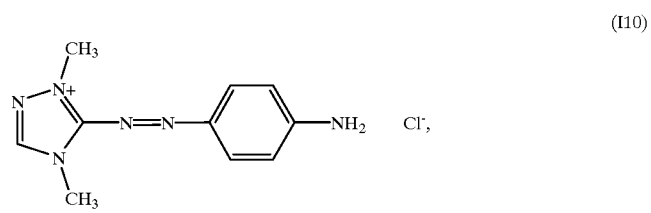
(I10)
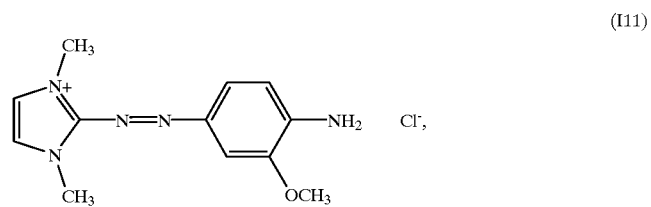
(I11)
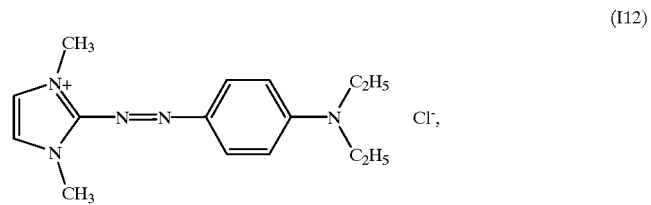
(I12)
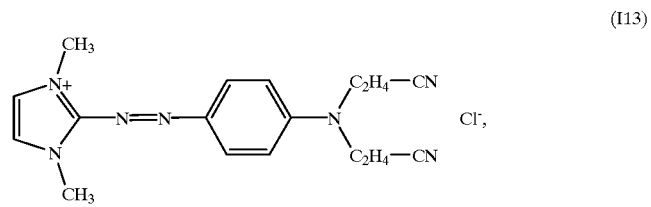
(I13)

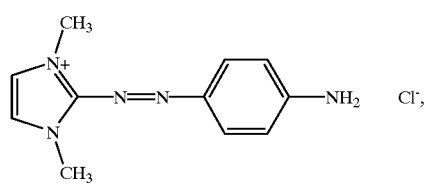
(I14)
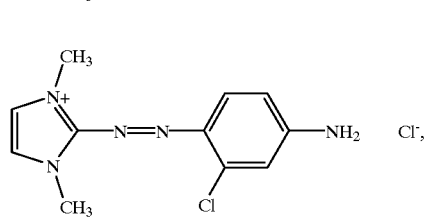
(I15)
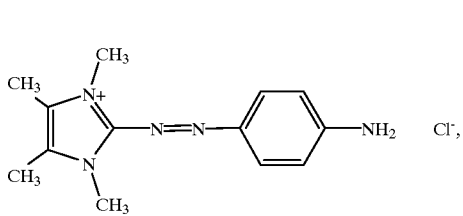
(I16)
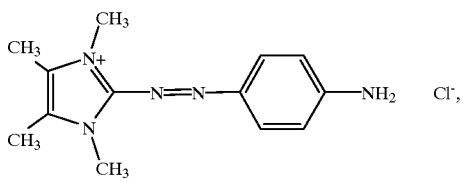
(I17)
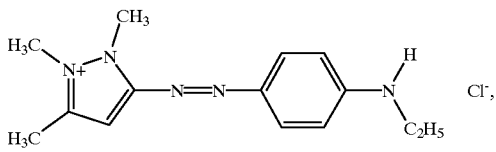
(I18)
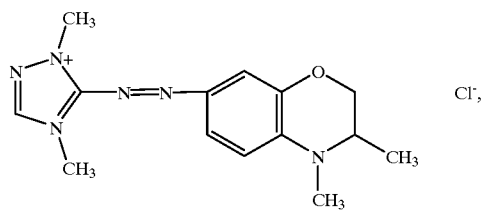
(I19)
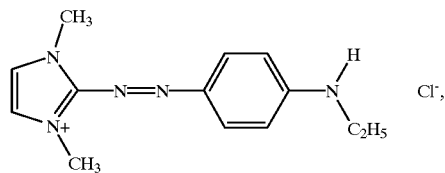
(I20)
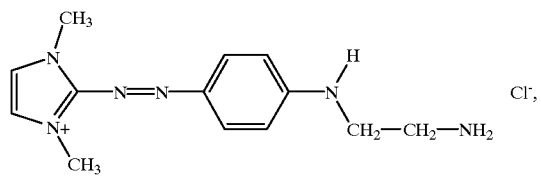
(I21)
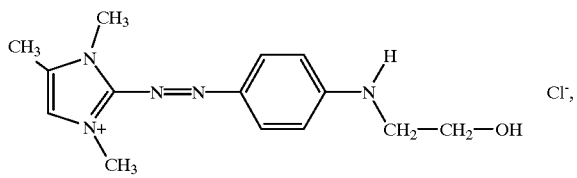

-continued
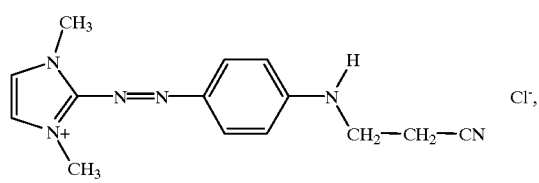
(I22) Cl⁻,
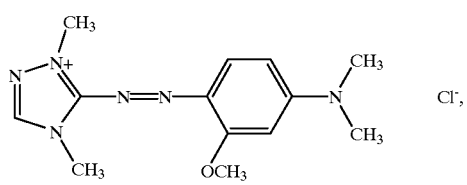
(I23) Cl⁻,
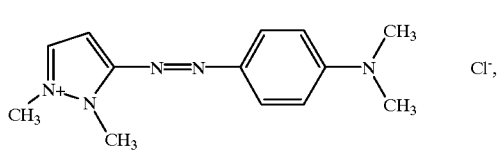
(I24) Cl⁻,
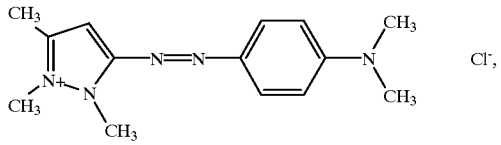
(I25) Cl⁻,
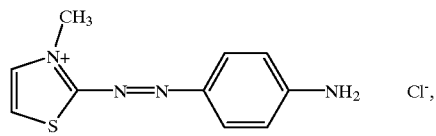
(I26) Cl⁻,
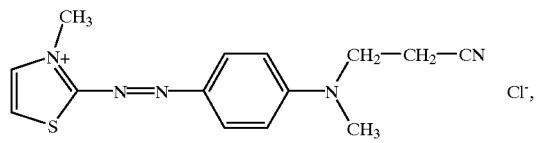
(I27) Cl⁻,
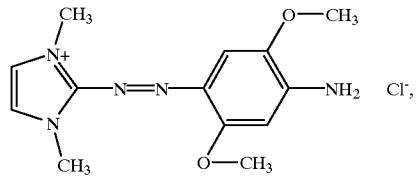
(I28) Cl⁻,
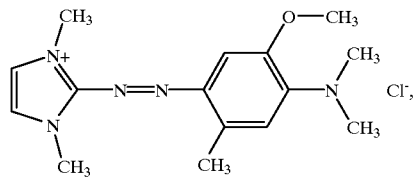
(I29) Cl⁻,
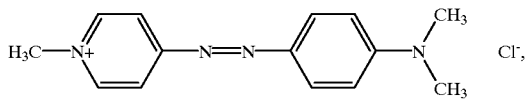
(I30) Cl⁻,

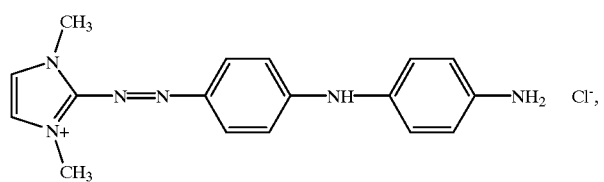
(I31)
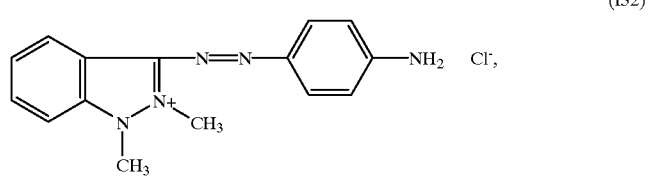
(I32)
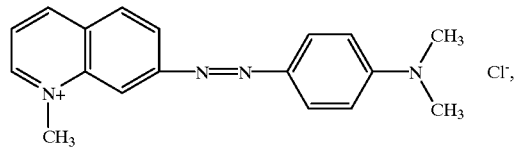
(I33)
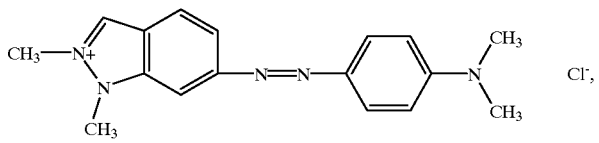
(I34)
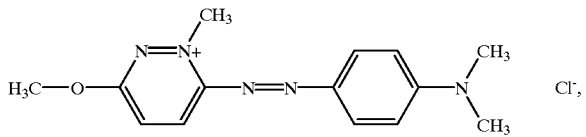
(I35)
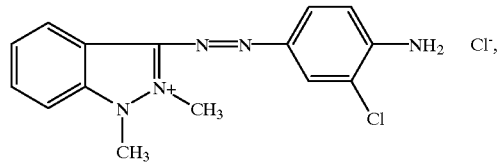
(I36)
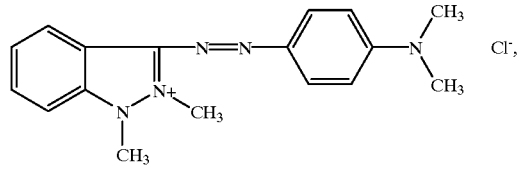
(I37)
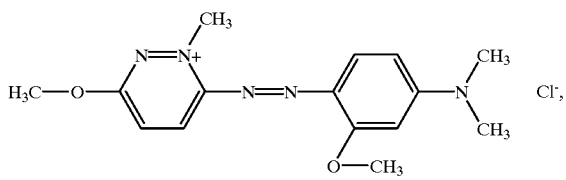
(I38)

-continued
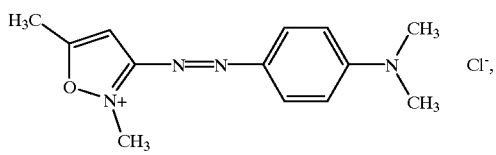 (I39)
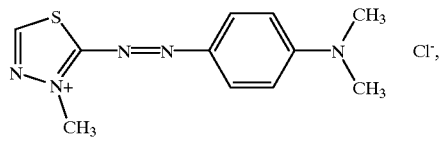 (I40)
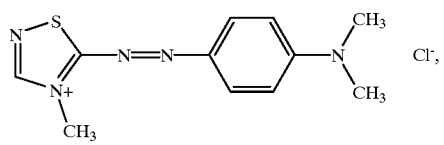 (I41)
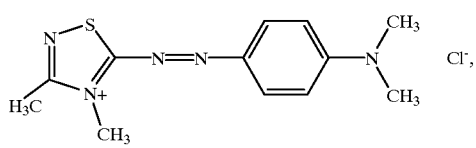 (I42)
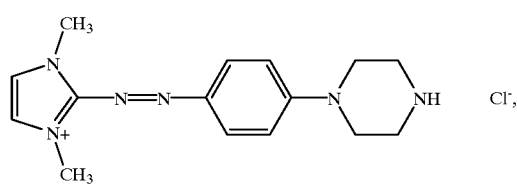 (I43)
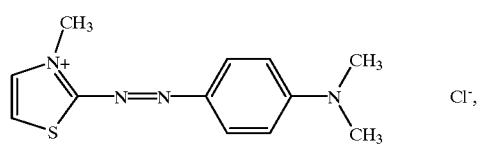 (I44)
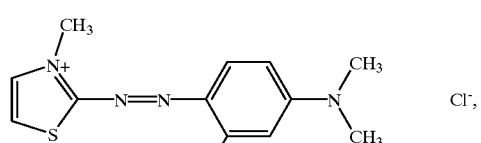 (I45)
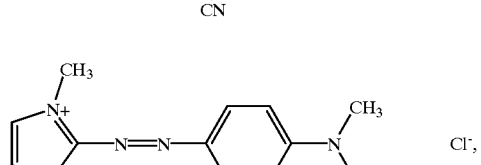 (I46)
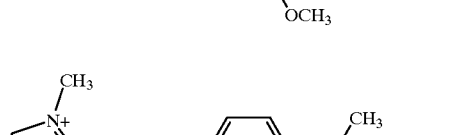 (I47)
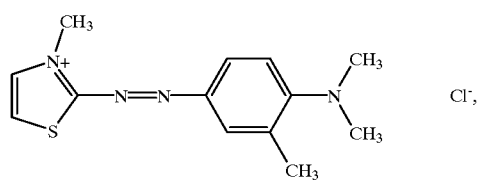

-continued

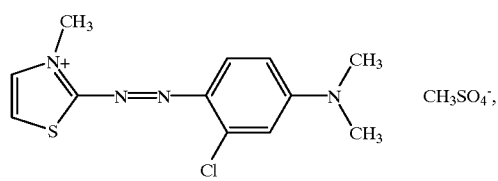 (I48)

CH₃SO₄⁻,

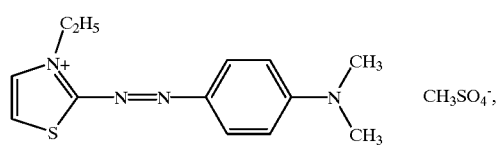 (I49)

CH₃SO₄⁻,

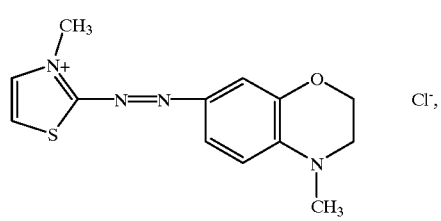 (I50)

Cl⁻,

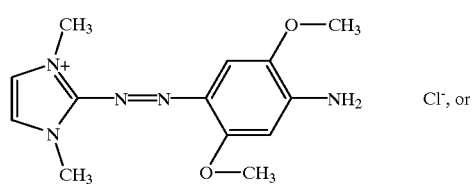 (I51)

Cl⁻, or

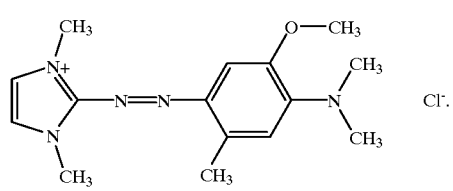 (I52)

Cl⁻.

18. A ready-to-use composition according to claim 17, wherein said at least one cationic direct dye of formula (I) is a compound corresponding to structure (I1), (I2), (I14) or (I31).

19. A ready-to-use composition according to claim 1, wherein said at least one cationic direct dye of formula (II) is a compound corresponding to one of structures (II1) to (II12):

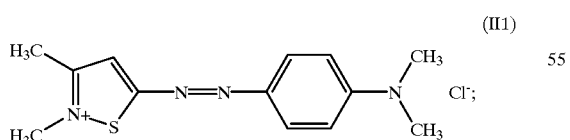 (II1)

Cl⁻;

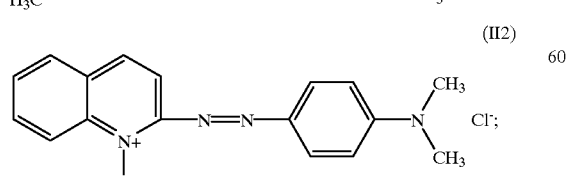 (II2)

Cl⁻;

-continued

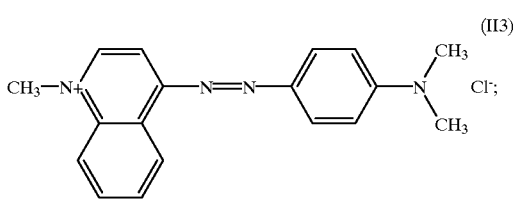 (II3)

Cl⁻;

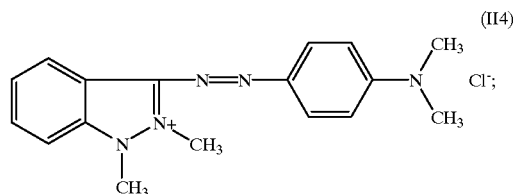 (II4)

Cl⁻;

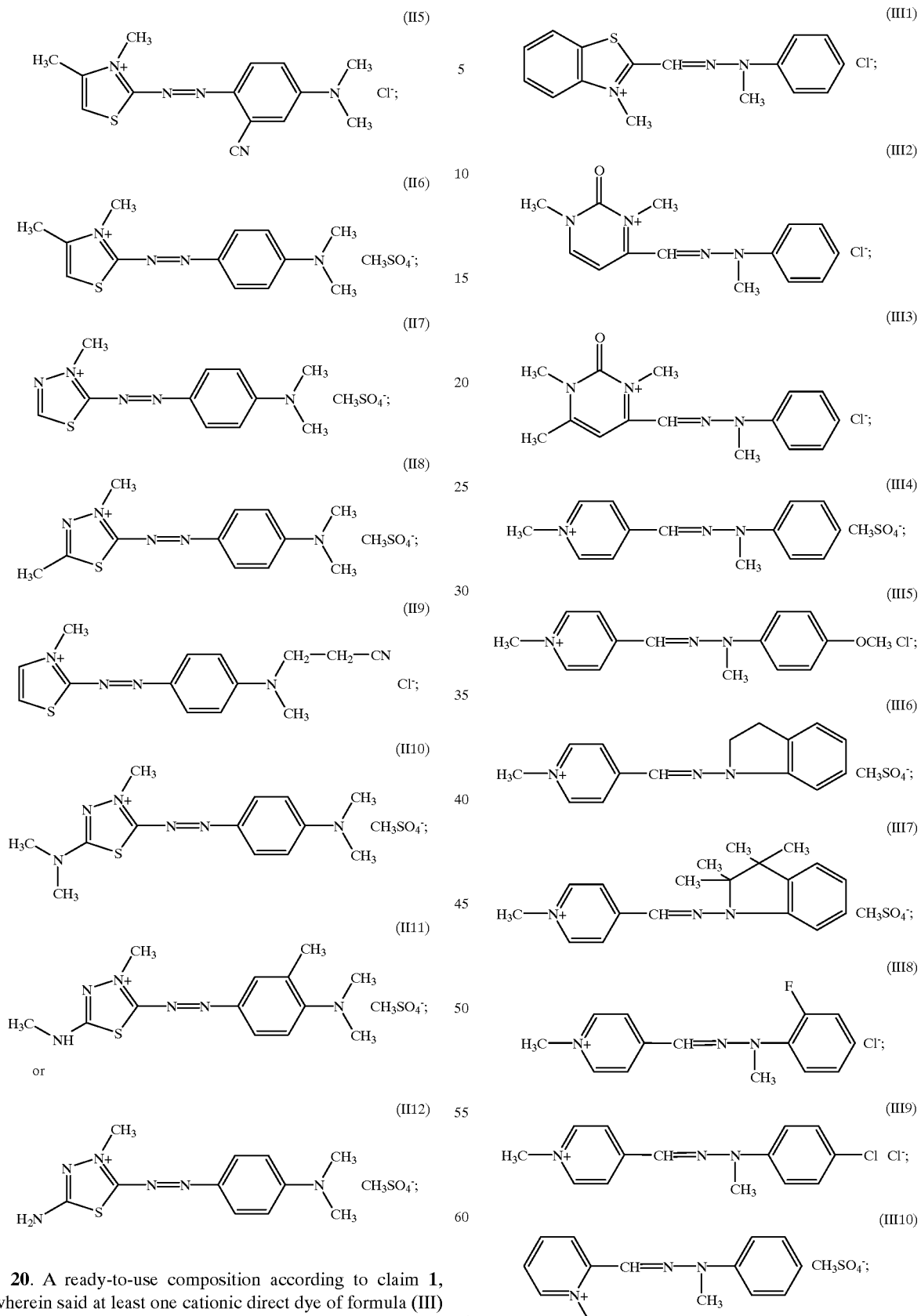
20. A ready-to-use composition according to claim 1, wherein said at least one cationic direct dye of formula (III) is a compound corresponding to one of structures (III1) to (III18):

(III11)
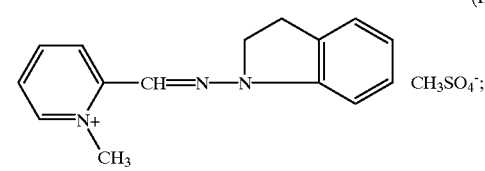

(III12)
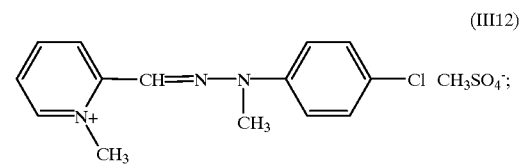

(III13)
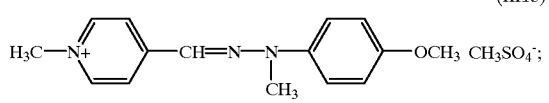

(III14)
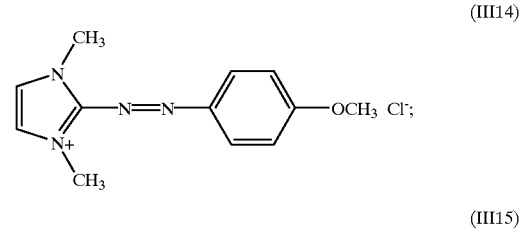

(III15)
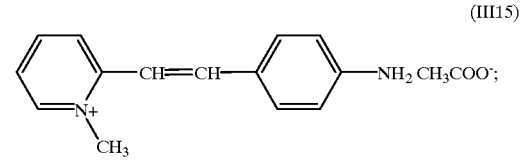

(III16)
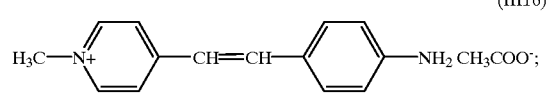

(III17)
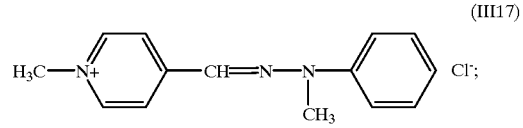

or (III18)
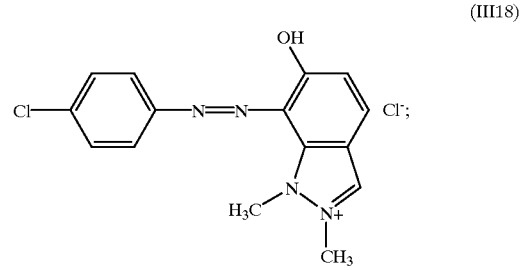

21. A ready-to-use composition according to claim 20, wherein said at least one cationic direct dye of formula (III) is a compound corresponding to one of structures (III4), (III5) or (III13).

22. A ready-to-use composition according to claim 1, wherein said at least one cationic direct dye of formula (III') is a compound corresponding to one of structures (III'1) to (III'3):

(III'1)
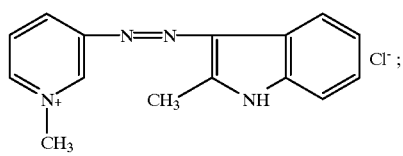

(III'2)
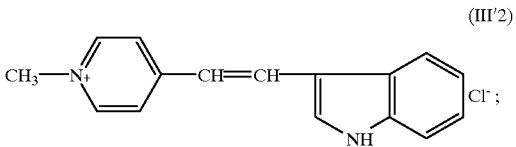

(III'3)
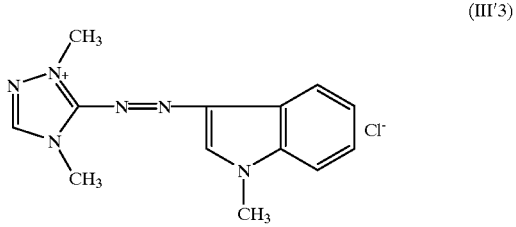

23. A ready-to-use composition according to claim 1, wherein said at least one oxidizing agent is hydrogen peroxide, urea peroxide, an alkali metal bromate or a persalt.

24. A ready-to-use composition according to claim 23, wherein said persalt is a perborate or a persulphate.

25. A ready-to-use composition according to claim 23, wherein said at least one oxidizing agent is hydrogen peroxide.

26. A ready-to-use composition according to claim 1, wherein said at least one oxidation base is present in a concentration ranging from 0.0001 to 10% by weight relative to the total weight of said ready-to-use composition.

27. A ready-to-use composition according to claim 1, wherein said at least one cationic direct dye is present in a concentration ranging from 0.001 to 10% by weight relative to the total weight of said ready-to-use composition.

28. A ready-to-use composition according to claim 1, wherein said ready-to-use composition has a pH ranging from 5 to 12.

29. A ready-to-use composition according to claim 1, wherein said medium suitable for dyeing comprises water or a mixture of water and at least one organic solvent.

30. A ready-to-use composition according to claim 1, wherein said ready-to-use composition further comprises at least one coupler.

31. A ready-to-use composition according to claim 30, wherein said at least one coupler is present in a concentration ranging from 0.0001 to 5% by weight, relative to the total weight of said ready-to-use composition.

32. A ready-to-use composition according to claim 1, wherein said ready-to-use composition is in the form of a liquid, a cream, a gel, or any form appropriate for dyeing keratin fibers.

33. A process for dyeing keratin fibers comprising applying at least one ready-to-use composition according to claim I to said keratin fibers.

34. A process for dyeing keratin fibers according to claim 33 wherein said keratin fibers are human hair.

35. A process for dyeing keratin fibers according to claim 33 wherein said ready-to-use dye composition is left on said keratin fibers for a time ranging from 3 to 40 minutes, and then is rinsed, optionally washed with shampoo, rinsed again and dried.

36. A process for dyeing keratin fibers according to claim 35, wherein said ready-to-use dye composition is left on said keratin fibers for a time ranging from 5 to 30 minutes.

37. A process for dyeing keratin fibers comprising:

applying at least one ready-to-use dye composition according to claim 1 to said keratin fibers, and further comprising the preliminary steps of:

preparing a composition (A) comprising, in a medium suitable for dyeing, at least one oxidation base according to claim 1 and at least one cationic direct dye according to claim 1, separately preparing a composition (B) comprising, in a medium suitable for dyeing, at least one oxidizing agent according to claim 1, separately storing composition (A) from composition (B), and mixing said composition (A) and said composition (B) together at the time of application before applying to said keratin fibers.

38. A process for dyeing keratin fibers comprising applying at least one ready-to-use dye composition according to claim 1 to said keratin fibers, and further comprising the preliminary steps of:

preparing a composition (A) comprising, in a medium suitable for dyeing, at least one oxidation base according to claim 1;

separately preparing a composition (A') comprising, in a medium which is suitable for dyeing, at least one cationic direct dye according to claim 1, separately preparing a composition (B) comprising, in a medium which is suitable for dyeing, at least one oxidizing agent according to claim 1, and mixing said composition (A), said composition (A'), and said composition (B) together at the time of application before applying to said keratin fibers.

39. A process according to claim 38, wherein said composition (A') is in powder form.

40. A multi-compartment dyeing kit or device, wherein said multi-compartment dyeing kit or device comprises a first compartment containing a composition (A) comprising, in a medium suitable for dyeing, at least one oxidation base according to claim 1 and at least one cationic direct dye according to claim 1, and a second compartment containing an oxidizing composition (B) comprising, in a medium suitable for dyeing, at least one oxidizing agent according to claim 1.

41. A multi-compartment dyeing kit or device, wherein said multi-compartment dyeing kit or device comprises a first compartment containing a composition (A) comprising, in a medium suitable for dyeing, at least one oxidation base according to claim 1, a second compartment containing a composition (A') comprising, in a medium which is suitable for dyeing, at least one cationic direct dye according to claim 1, and a third compartment containing an oxidizing composition (B) comprising, in a medium which is suitable for dyeing, at least one oxidizing agent according to claim 1.

* * * * *

UNITED STATES PATENT AND TRADEMARK OFFICE
CERTIFICATE OF CORRECTION

PATENT NO. : 6,001,135
DATED : December 14, 1999
INVENTOR(S) : RONDEAU et al.

It is certified that error appears in the above-identified patent and that said Letters Patent is hereby corrected as shown below:

Title page, item [75], line 2, "Verneuil Sur Seine" should read --Verneuil-sur-Seine--;

line 3, "De La" should read --de la--; and

"Vesinet" should read --Vésinet--.

Title page, item [73], in the Assignee, "L'Oreal" should read --L'Oréal--.

In claim 14, column 34, line 14, "salts" should read --salt--.

In claim 17, column 35, in structure (I8):

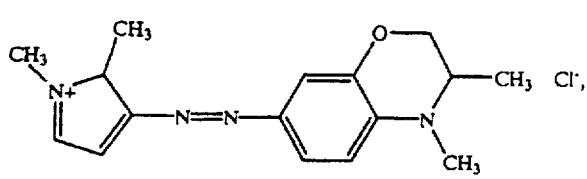

should read

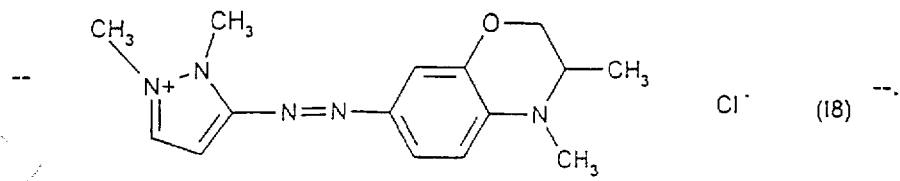

UNITED STATES PATENT AND TRADEMARK OFFICE
CERTIFICATE OF CORRECTION

PATENT NO. : 6,001,135

DATED : December 14, 1999

INVENTOR(S) : RONDEAU et al.

It is certified that error appears in the above-identified patent and that said Letters Patent is hereby corrected as shown below:

In claim 17, column 35, in structure (I9):

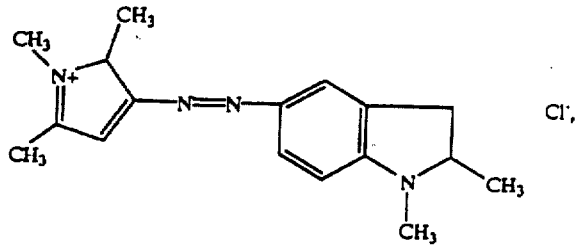

should read

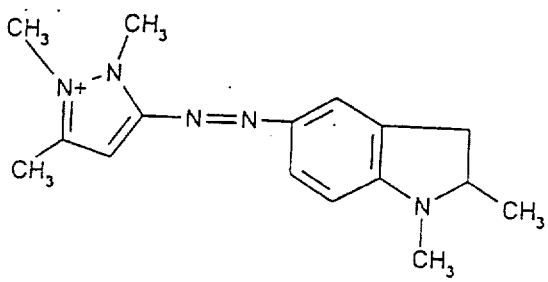

UNITED STATES PATENT AND TRADEMARK OFFICE
CERTIFICATE OF CORRECTION

PATENT NO. : 6,001,135

DATED : December 14, 1999

INVENTOR(S) : RONDEAU et al.

Page 3 of 3

It is certified that error appears in the above-identified patent and that said Letters Patent is hereby corrected as shown below:

In claim 17, column 37, in structure (I18):

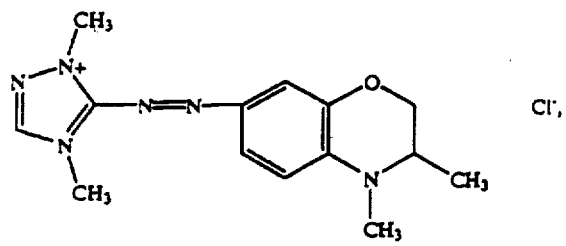

should read:

-- 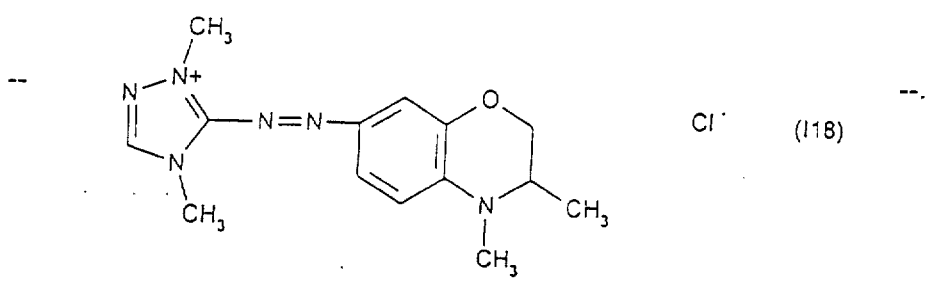 --.

UNITED STATES PATENT AND TRADEMARK OFFICE
CERTIFICATE OF CORRECTION

PATENT NO. : 6,001,135
DATED : December 14, 1999
INVENTOR(S) : Rondeau et al

It is certified that error appears in the above-identified patent and that said Letters Patent is hereby corrected as shown below:

In claim 22, column 50, between structures (III'2) and (III'3), insert the term --or--.

In claim 33, column 50, lines 57-58, "claim I" should read --claim 1--.

Signed and Sealed this

Twenty-sixth Day of September, 2000

Attest:

Q. TODD DICKINSON

*Attesting Officer*　　　　　*Director of Patents and Trademarks*